(12) United States Patent
Daniel

(10) Patent No.: US 11,819,671 B2
(45) Date of Patent: Nov. 21, 2023

(54) MEDICAMENT DELIVERY DEVICE

(71) Applicant: SHL MEDICAL AG, Zug (CH)

(72) Inventor: Mattias Daniel, Stockholm (SE)

(73) Assignee: SHL MEDICAL AG, Zug (CH)

(*) Notice: Subject to any disclaimer, the term of this patent is extended or adjusted under 35 U.S.C. 154(b) by 57 days.

(21) Appl. No.: 17/518,139

(22) Filed: Nov. 3, 2021

(65) Prior Publication Data
US 2022/0054759 A1 Feb. 24, 2022

Related U.S. Application Data

(63) Continuation of application No. 17/323,382, filed on May 18, 2021, which is a continuation of application
(Continued)

(30) Foreign Application Priority Data

Mar. 31, 2010 (SE) .................................. 1050307-6

(51) Int. Cl.
*A61M 5/315* (2006.01)
*A61M 5/20* (2006.01)
(Continued)

(52) U.S. Cl.
CPC ............ *A61M 5/3157* (2013.01); *A61M 5/20* (2013.01); *A61M 5/2033* (2013.01); *A61M 5/24* (2013.01);
(Continued)

(58) Field of Classification Search
CPC .......... A61M 5/3243; A61M 2005/208; A61M 5/3157; A61M 5/20; A61M 5/2033;
(Continued)

(56) References Cited

U.S. PATENT DOCUMENTS 6,454,743 B1 9/2002 Weber
6,638,255 B1 10/2003 Weber
(Continued)

FOREIGN PATENT DOCUMENTS

DE 102004052219 5/2006
EP 0937472 8/1999
(Continued)

OTHER PUBLICATIONS

International Search Report and Written Opinion for Int. App. No. PCT/SE2011/050326, dated Jul. 13, 2011.
(Continued)

*Primary Examiner* — Kevin C Sirmons
*Assistant Examiner* — Leah J Swanson
(74) *Attorney, Agent, or Firm* — MCDONNELL BOEHNEN HULBERT & BERGHOFF LLP

(57) ABSTRACT

A medicament delivery device is presented having a drive configured to act on a medicament container for expelling a medicament; a holder configured to hold said drive in a pre-tensioned state; an activator configured to interact with said holder for releasing said drive from the pre-tensioned state; wherein the device further includes a feedback mechanism configured to interact both with said holder and with said drive for generating an audible and/or tactile and/or visual signal indicating that the medicament has been completely expelled.

13 Claims, 10 Drawing Sheets

Related U.S. Application Data

No. 17/114,241, filed on Dec. 7, 2020, which is a continuation of application No. 15/994,381, filed on May 31, 2018, now Pat. No. 10,933,197, which is a continuation of application No. 15/480,820, filed on Apr. 6, 2017, now abandoned, which is a continuation of application No. 13/650,708, filed on Oct. 12, 2012, now Pat. No. 9,662,452, which is a continuation of application No. 13/636,241, filed as application No. PCT/SE2011/050326 on Mar. 23, 2011, now Pat. No. 9,199,038.

(60) Provisional application No. 61/319,453, filed on Mar. 31, 2010.

(51) Int. Cl.
    *A61M 5/24*          (2006.01)
    *A61M 5/32*          (2006.01)

(52) U.S. Cl.
    CPC ...... *A61M 5/3158* (2013.01); *A61M 5/31501* (2013.01); *A61M 5/31511* (2013.01); *A61M 5/31515* (2013.01); *A61M 5/31585* (2013.01); *A61M 5/3243* (2013.01); *H05K 999/99* (2013.01); *A61M 5/3202* (2013.01); *A61M 2005/208* (2013.01); *A61M 2005/2013* (2013.01); *A61M 2005/2485* (2013.01); *A61M 2205/581* (2013.01); *A61M 2205/582* (2013.01); *A61M 2205/583* (2013.01); *A61M 2205/584* (2013.01)

(58) Field of Classification Search
    CPC .. A61M 5/24; A61M 5/31511; A61M 5/3202; A61M 5/31501; A61M 5/31515; A61M 5/3158; A61M 5/31585; A61M 2005/2013; A61M 2005/2485; A61M 2005/2073; A61M 2005/3258; A61M 2005/3261; A61M 2005/3263; A61M 2005/3264; A61M 2005/3265; A61M 2005/3267; A61M 2005/3268; A61M 5/3245; A61M 5/3257; A61M 5/326; A61M 5/3269; A61M 5/3271; A61M 5/3272; A61M 5/3273; A61M 5/3275; A61M 2205/581–583; A61M 2005/2403; A61M 2005/2433–2444; A61M 2005/3247; A61M 5/2422; A61M 5/3205; A61M 5/321; A61M 5/50; A61M 2205/27–273

See application file for complete search history.

(56) References Cited

U.S. PATENT DOCUMENTS

| | | |
|---|---|---|
| 2002/0004648 A1 | 1/2002 | Larsen et al. |
| 2005/0027255 A1 | 2/2005 | Lavi et al. |
| 2005/0277886 A1 | 12/2005 | Hommann et al. |
| 2006/0189933 A1 | 8/2006 | Alheidt et al. |
| 2008/0262438 A1 | 10/2008 | Bollenbach et al. |
| 2009/0149809 A1 | 6/2009 | Bollenbach et al. |
| 2009/0312705 A1 | 12/2009 | Grunhut et al. |
| 2010/0152659 A1 | 6/2010 | Streit et al. |
| 2012/0209192 A1 | 8/2012 | Alexandersson |

FOREIGN PATENT DOCUMENTS

| | | | | |
|---|---|---|---|---|
| EP | 1349590 | 5/2006 | | |
| EP | 1923083 | 5/2008 | | |
| WO | 2005/113039 | 12/2005 | | |
| WO | WO-2008047372 A2 * | 4/2008 | .......... | A61M 5/2033 |
| WO | 2008/113864 | 9/2008 | | |
| WO | 2009/040602 | 4/2009 | | |
| WO | WO-2009040602 A1 * | 4/2009 | .......... | A61M 5/2033 |
| WO | WO-2009153542 A1 * | 12/2009 | ............ | A61J 1/2096 |

OTHER PUBLICATIONS

Mosimann et al.; Machine English Translation of WO 2008113864; Sep. 2008; Translation obtained Jun. 9, 2016.

* cited by examiner

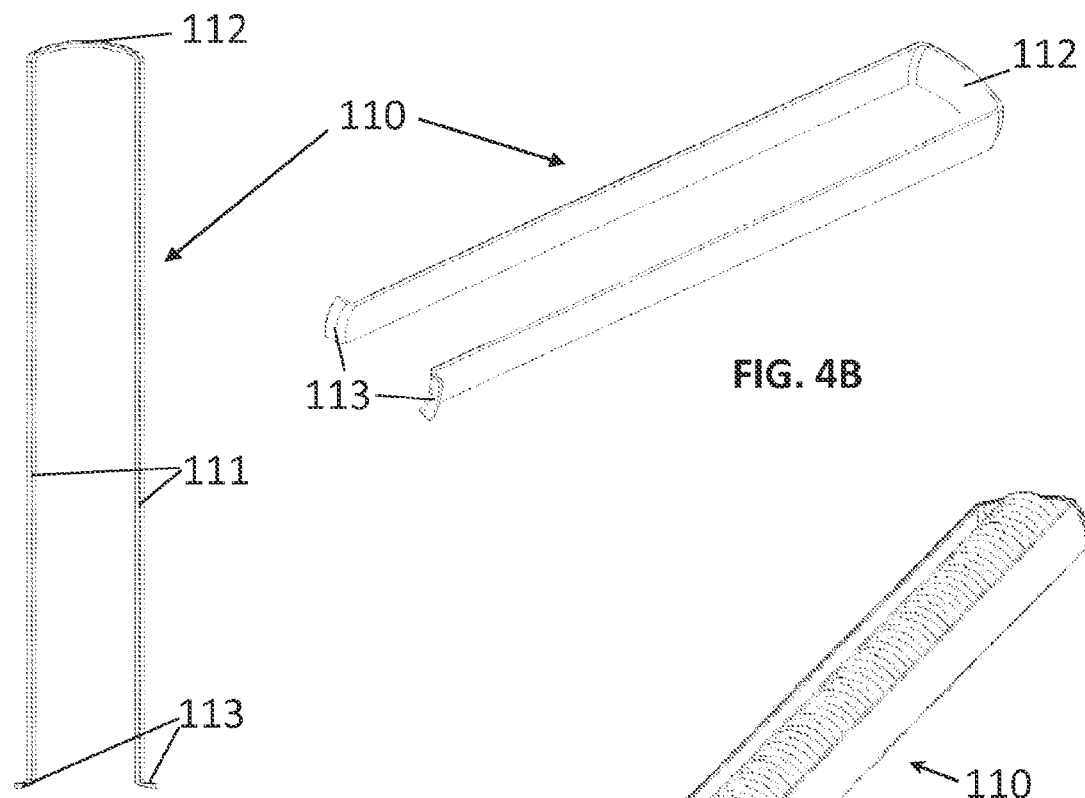
FIG. 4A
FIG. 4B
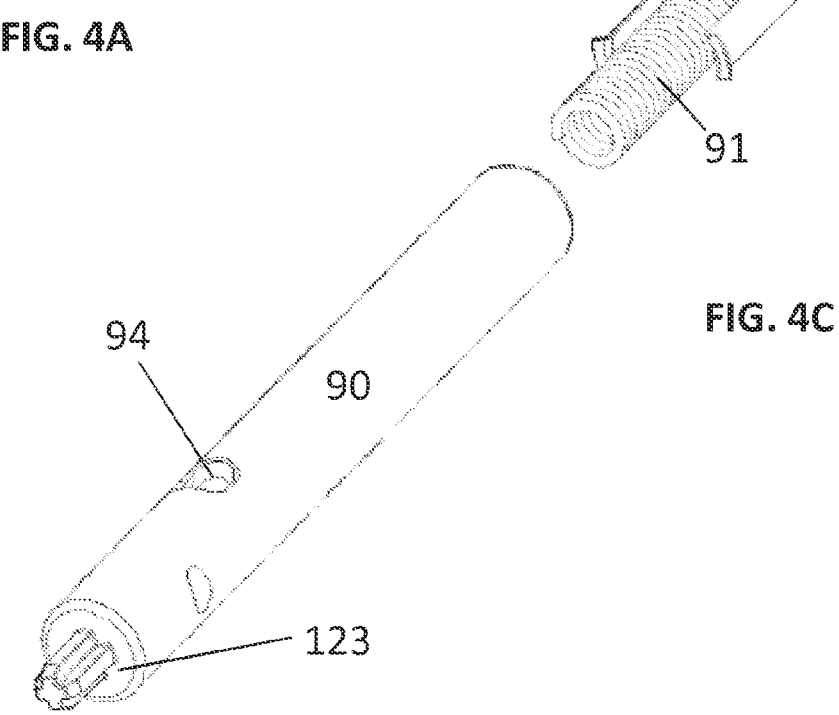
FIG. 4C

MEDICAMENT DELIVERY DEVICE

CROSS REFERENCE TO RELATED APPLICATIONS

The present application is a continuation U.S. patent application Ser. No. 17/323,382, filed May 18, 2021, which is a continuation of U.S. patent application Ser. No. 17/114,241, filed Dec. 7, 2020, which is a continuation of U.S. patent application Ser. No. 15/994,381, filed May 31, 2018, now U.S. Pat. No. 10,933,197, which is a continuation of U.S. patent application Ser. No. 15/480,820, filed Apr. 6, 2017, which is a continuation of U.S. patent application Ser. No. 13/650,708, filed Oct. 12, 2012, now U.S. Pat. No. 9,662,452, which is a continuation of U.S. patent application Ser. No. 13/636,241 filed Oct. 12, 2012, now U.S. Pat. No. 9,199,038, which is a U.S. National Phase Application pursuant to 35 U.S.C. § 371 of International Application No. PCT/SE2011/050236 PCT/SE2011/050326 filed Mar. 23, 2011, which claims priority to U.S. Patent Application No. 61/319,453 filed Mar. 31, 2010 and Swedish Patent Application No. 1050307-6 filed on Mar. 31, 2010. The entire disclosure contents of these applications are herewith incorporated by reference into the present application.

FIELD OF INVENTION

The present invention relates to a medicament delivery device and in particular to an improved, more user-friendly, automatic medicament delivery device providing an audible, tactile or visual confirmation to a user when an injection has been made.

BACKGROUND

Many medicament delivery devices are developed for self-administration, i.e. a user performs the medicament delivery her-, or himself. This requires a medicament delivery device which is as safe to use and as easy to handle as possible. In order to meet these requirements, the risk of human errors must be minimized, the number of actions needed to be performed in order to receive a dose need to be reduced and the device must be intuitive and ergonomic to use. Thus, in order to minimize the risk of human errors, it is desirable to have the device as pre-assembled as possible.

Document EP 1349590 B describes an injector having a number of features that facilitate the handling of the injector. The penetration and injection is performed manually by simply pressing the proximal end of a needle shield against the delivery area, causing the shield to move in a distal direction, enabling the needle to penetrate the injection area and thereafter initialize the injection process. When the injection is performed the injector is withdrawn whereby a needle shield extracts around the needle in a locked way.

Other aspects of injectors are the human aspect of handling the injector regarding how it is held during operation. a general aim is to have the patient holding the injector in an ergonomic way that may permit the penetration and injection in different locations on the body, such as around the waist and also on the backside of the waist and/or in the buttocks of the patient. Sometimes the patient does not see the injector at those locations and need to be able to hold the injector without having to change grip. By removing the action of pushing a button or the like, the patient is free to hold the device as he desires and feels comfortable.

It is considered important for the patient to receive a confirmation that the injection has been made, in particular in instances when an injector is used where the patient does not see the injector, e.g. such as around the waist and also on the backside of the waist and/or in the buttocks of the patient.

SUMMARY

The object of the present invention is to provide a medicament delivery device that is reliable and easy to use when handling and activating, this is achieved by a medicament delivery device comprising a drive means configured to act on a medicament container for expelling a medicament; a holding means configured to hold said drive means in a pre-tensioned state; an activation means configured to interact with said holding means for releasing said drive means from the pre-tensioned state; wherein the device further comprises feedback means configured to interact both with said holding means and with said drive means for generating an audible and/or tactile and/or visual signal indicating that the medicament has been completely expelled.

According to another aspect of the invention the device further comprises a tubular housing having a proximal end and an opposite distal end.

According to a further aspect of the invention the activation means is a tubular activation member slidably and coaxially arranged in relation to the tubular housing.

According to yet another aspect of the invention the device further comprises a container holder coaxially arranged within the tubular activation member and fixedly attached to the tubular housing.

According to yet a further aspect of the invention the medicament container is arranged within said container holder and wherein said medicament container comprises a predetermined volume of medicament, a slidable stopper and a delivery member.

According to yet an aspect of the invention the drive means comprises a plunger rod and a first resilient member which is pre-tensioned arranged within the plunger rod and wherein said plunger rod is arranged to be in contact with the slidable stopper within the medicament container.

According to another aspect of the invention the holding means are a tubular extension part fixedly connected to the distal end of the tubular housing and a tubular operation member which is interactively connected both to the tubular extension part and to the tubular activation member, such that when said tubular activation member is pressed against a delivery site said tubular operation member is rotated in relation to said tubular extension part whereby said drive means are released from the pre-tensioned state for exerting a pressure on the slidable stopper and thereby expelling the medicament.

According to a further aspect of the invention the feedback means is a longitudinally extending signal generating member interactively connected to said tubular extension part and to said drive means, such that when the plunger rod is completely released from the tubular extension part and the longitudinally extending signal generating member, the longitudinally extending signal generating member is released from said tubular extension part and displaced distally by a remaining force of the first resilient member for generating an audible and/or tactile and/or visual signal indicating that the medicament has been completely expelled.

According to a still further aspect of the invention, the tubular operation member comprises a first co-acting means interactively connected to a corresponding first co-acting means of the tubular activation member and a second co-acting means interactively connected to a corresponding second co-acting means of the tubular extension part; the plunger rod comprises a releasable engaging means interactively connected to the corresponding second co-acting means of the tubular extension part and a proximal end wall being in contact with the slidable stopper; the longitudinally extending signal generating member is releasable arranged on an inner surface of the tubular extension part; and wherein the first resilient member has a first end abutting the proximal end wall of the plunger rod and a second end abutting a transversal wall of the signal generating member.

According to another aspect of the invention, the second co-acting means comprises a groove on an inner surface of the tubular operation member and the corresponding second co-acting means of the tubular extension part comprises a resilient tongue, having a radial inward protrusion.

According to a yet another aspect of the invention, the releasable engaging means comprises a groove on an outer surface of the plunger rod releasable engaged to the radial inward protrusion of the resilient tongue adapted to hold the drive means in the pre-tensioned state.

According to a yet a further aspect of the invention, the first co-acting means comprise a groove on an outer surface of the tubular operation member and the first corresponding co-acting means comprise a radial inward extending protrusion on the distal end of the inner surface of the tubular activation member, such that the radial inward extending protrusion is adapted to be guided within the groove on an outer surface of the tubular operation member forcing the tubular operation member to rotate when the tubular activation member is distally moved, whereby the resilient tongue is flexed radial outward into a groove on the inner surface of the tubular operation member and the radial inward extended protrusion is disengaged from the groove on the outer surface of the plunger rod such that the drive means are released from the pre-tensioned state.

According to another aspect of the invention, the signal generating member is an elongated u-shaped bracket comprising a transversal wall and two longitudinally extending flexible arms provided with angled support members extending radially outward, and wherein said support members are adapted to rest on an annular proximal end of the tubular extension part when the drive means are in the pre-tensioned state.

According to a further aspect of the invention, the transversal wall of the U-bracket is arranged at a predetermined distance D from an inner distal surface of said tubular extension part when the drive means are in the pre-tensioned state.

According to yet another aspect of the invention, the audible signal is generated for confirming that a medicament delivery has been performed when the distal end of the plunger rod has passed the supporting members, such that the longitudinally extending flexible arms, with the support members, are released and allowed to move in a radial inward direction, enabling the U-bracket to move the predetermined distance D in the distal direction by a remaining force exerted by said first resilient member, whereby the transversal wall of the bracket hits the inner distal surface of said tubular extension part.

According to yet a further aspect of the invention, the transversal wall of the U-bracket comprises a distally extending protrusion and the distal surface of the tubular extension part comprises a through hole, such that when the transversal wall of the U-bracket hits the inner distal surface of said tubular extension part, the distally extending protrusion passes through the through hole and extends distally a predetermined distance over the outer surface of said tubular extension part for generating a tactile signal.

According to another aspect of the invention, the distally extending protrusion has a bright and/or different colour than the rest of the device for generating a visual signal.

By the term automatic medicament delivery device, is herein meant a medicament delivery device adapted to deliver a medicament without a user having to press a push button or activation member, but instead only by pressing the proximal end of the medicament delivery device against the delivery site.

In automatic medicament delivery device it is considered, as mentioned above, important for the patient to receive a confirmation that the delivery has been made, in particular when the medicament delivery device is used where the patient does not see the medicament delivery device, e.g. such as around the waist and also on the backside of the waist and/or in the buttocks of the patient. Therefore, a signal i.e. an audible sound, and/or a tactile signal, and/or a visual signal, or a combination thereof is generated in direct temporal relationship to the physical actuation of the medicament container, in order to expel the medicament from the medicament container.

The medicament delivery device according to the present invention presents a number of advantages. There is a high degree of functionality and automation, which remove unnecessary components and actions for delivering a medicament.

Also an important safety aspect is met since, during withdrawal, the tubular activation member is pushed out and covers the delivery member e.g. a needle, and also locks in the extended state, thereby preventing unintentional needle sticks.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

FIGS. 4a, 4b and 4c illustrate the components of the audio-tacit-visual signal signal generating member-, and plunger rod assembly.

DETAILED DESCRIPTION

In the present application, when the term "distal part/end" is used, this refers to the part/end of the delivery device, or the parts/ends of the members thereof, which is/are located the furthest away from the medicament delivery site of the patient. Correspondingly, when the term "proximal part/end" is used, this refers to the part/end of the delivery device, or the parts/ends of the members thereof, which, is/are located closest to the medicament delivery site of the patient.

Figure 1A:
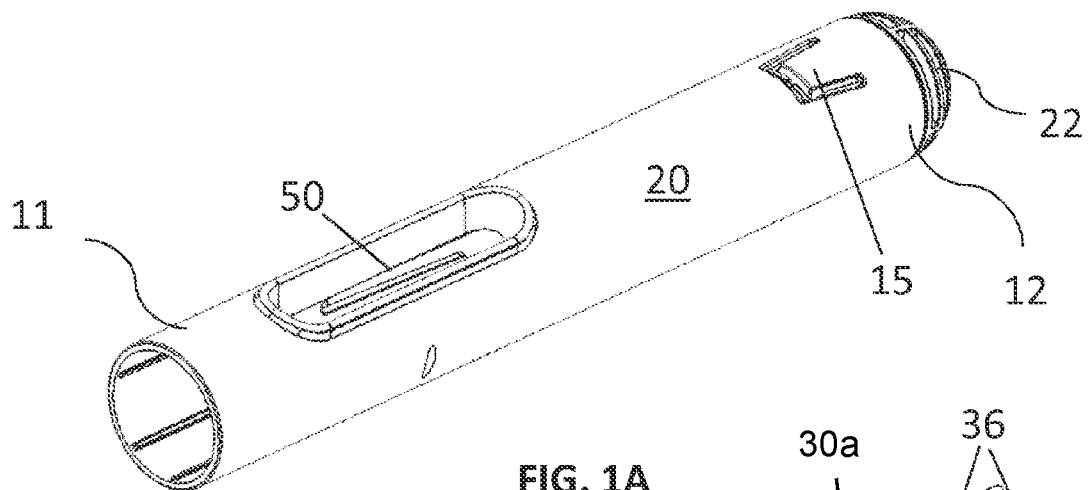
FIGS. 1a, 1b and 1c show perspective views of different components of the medicament delivery device.

FIG. 1a illustrates, in perspective, a tubular housing 20 of an exemplary medicament delivery device 1. The tubular housing 20 having a proximal end 11 and an opposite distal end 12. The tubular housing 20 further comprises a protrusion (not illustrated) on its inner wall. The protrusion is adapted for receiving a recess 36 of an activation means, such as a tubular activation member 30 (see FIG. 1b). The recess 36 of the tubular activation member 30 is used for locking the tubular activation member 30, inside the tubular housing 20, when the tubular activation member 30 is in its most proximal position, after an injection has been made. In an exemplary embodiment there are two protrusions (not illustrated), one on each side of the inner wall of the tubular housing 20, and correspondingly two recesses 36 of the tubular activation member 30. The tubular housing 20 further comprises a container holder 50 which is coaxially arranged and fixedly attached within the tubular housing 20 for lodging a medicament container 80 (see FIG. 1c). The medicament injection device 1 further comprises a tubular extension part 22, being coaxially arranged and fixedly attached to the distal end 12 of the housing preferably by a flexible tongue engaging with a corresponding ledge 23 (see FIG. 5) of the tubular extension part 22.

Figure 1B:
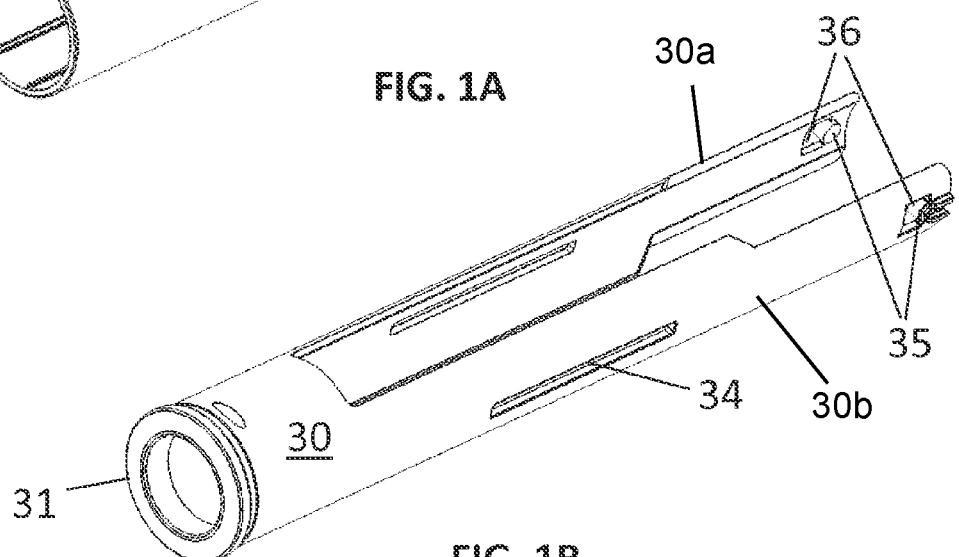

FIG. 1B illustrates the tubular activation member 30 of the medicament injection device 1. The tubular activation member 30 having an annular contact member, exemplified in FIG. 1B as a radial flange 31, two distally projecting arms 30a & 30b, and a corresponding first co-acting means 35, which in an exemplary embodiment is a protrusion. In an exemplary embodiment of the invention there are two corresponding first co-acting means 35 which are used for activating the medicament delivery device 1 as will be described in detail below. In the figure is in particular illustrated a guiding means 34 which is adapted to cooperate with a corresponding guiding rod (not shown) at the interior of the tubular housing 20, with the purpose to prevent that the tubular activation member 30 may rotate in relation to the tubular housing 20 and to allow the tubular activation member 30 to move in the axial direction in relation to the tubular housing 20. In a preferred embodiment of the invention there are two guiding means 34 and correspondingly two guiding rods (not shown). According to an embodiment of the invention, a second resilient member 24 (see FIG. 1c), which in an exemplary embodiment is a tension spring, is arranged at the proximal end of the tubular activation member 30 for moving it in a proximal direction. The cut-out/recess 36 is, when the medicament injection device 1 is positioned in its final position in order to prevent unintentional availability of a proximal needle end 61 (see FIG. 1c), engaging with a corresponding protrusion (not illustrated) of the tubular housing 20.

Figure 1C:
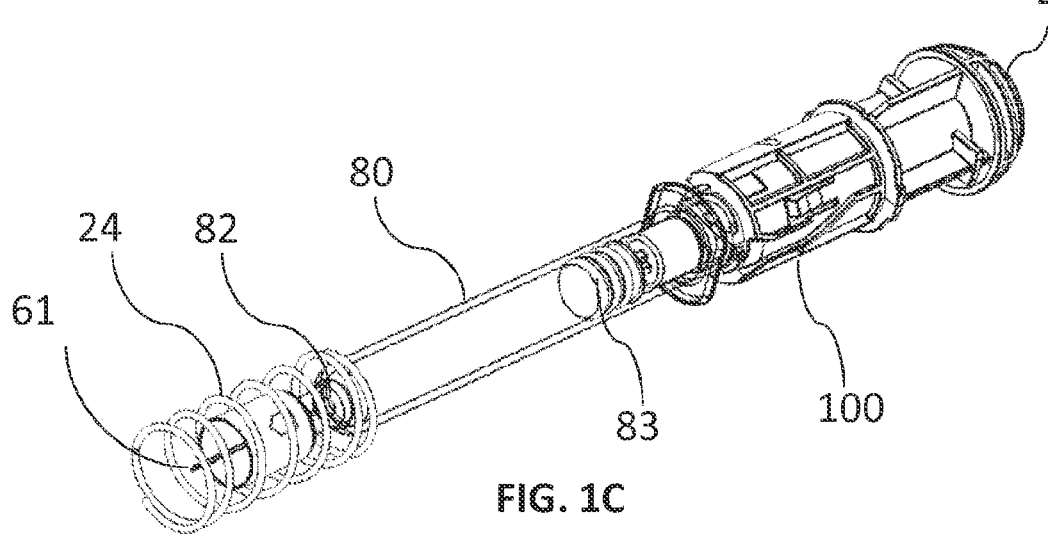

FIG. 1c illustrates the interior of the medicament delivery device 1 further comprising the second resilient member 24 arranged in relation to the tubular activation member for moving it in a proximal direction from a non-activated position to an activated position whereby the annular contact member 31 is in contact with the proximal end of the housing 20 when the medicament injection device 1 is in non-activated state and whereby the annular contact member 31 is at a predetermined distance from the proximal end of the housing when the medicament injection device 1 is in activated state. The medicament container 80 is arranged within the container holder 50 and has a predetermined volume of medicament, a slidable stopper 83 and a delivery member. In an exemplary embodiment of the invention the medicament container 80 is a syringe provided with a needle 61 as the delivery member, however the invention should not be limited to this, other embodiments could include a medicament cartridge having a membrane 82, or the like where a delivery member can be adapted. In the medicament delivery device 1 is also included a tubular operation member 100 (see FIG. 5) comprising a second co-acting means 101, 102, 103 interactively connected to a corresponding first co-acting means 35 of the tubular activation member 30 (see FIG. 1b), drive means comprising a plunger rod 90 and a first resilient member 91 arranged within the plunger rod. The plunger rod comprises a releasable engaging means 94 as a cut-out/recess (see FIG. 4c) interactively connected to a corresponding second co-acting means 121 (see FIG. 5) of the tubular extension part 22. The first resilient member 91 is in an exemplary embodiment of the invention a tension spring. The proximal end 92 of the plunger rod 90 is in contact with the slidable stopper 83. The tubular operation member 100 (see FIG. 5) is rotatably and coaxially arranged on a proximal part of the tubular extension part 22 between the container holder 50 and an annular ledge of the tubular extension part 22 at the distal end of the tubular housing 20.

Together, the tubular extension part 22 and the tubular operation member 100 form a holding means, for holding the drive means in a pre-tensioned state prior to penetration. Upon actuation of the activation means a feedback means interacts with the holding means and the drive means to signal that a medicament has been completely expelled.

Figure 2A:
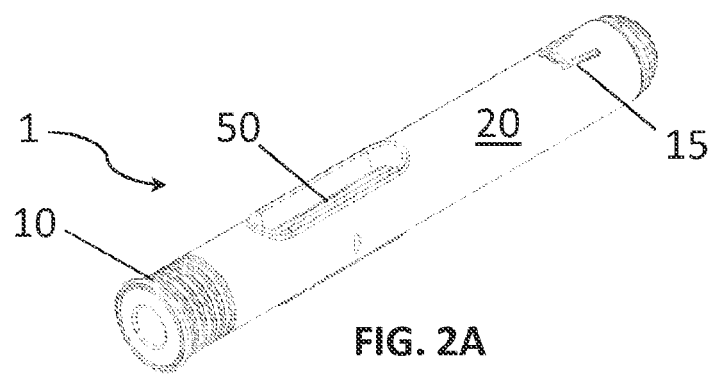
FIGS. 2a, 2b, 2c and 2d show perspective views of different states of the medicament delivery device.
Figure 2B:
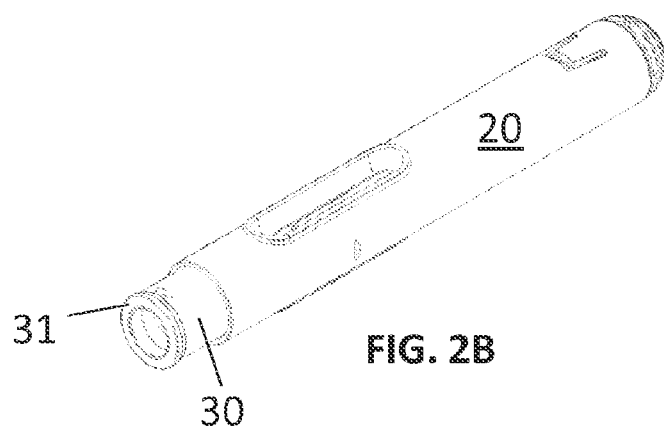
Figure 2C:
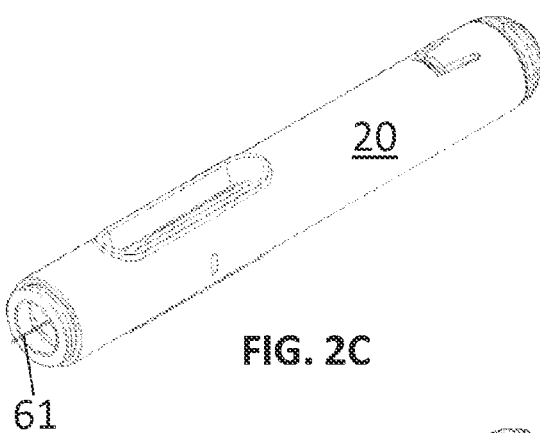
Figure 2D:
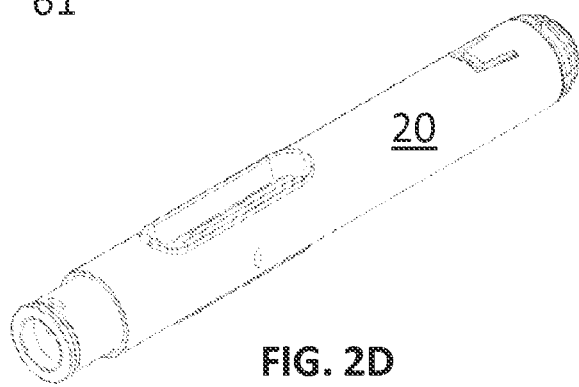

FIG. 2a-FIG. 2d show simplified perspective views of the medicament delivery device 1, where FIG. 2a illustrates an initial, non-activated, state of the medicament delivery device 1 having a cap 10. FIG. 2b shows an activated state of the medicament delivery device 1, where the cap 10 is removed. FIG. 2c shows the penetration and injection state of the medicament delivery device 1 and finally FIG. 2d shows the medicament delivery device 1 in a final locked state. With references to FIG. 2a, the medicament delivery device 1 comprises the tubular housing 20, having a proximal end and an opposite distal end. The medicament injection device 1 further comprises the tubular activation member 30 which is slidably and coaxially arranged inside the tubular housing 20 and comprises the proximal annular contact member 31. The cap 10 comprises a distal end surface, abutting with the proximal end surface of the annular contact member 31 of the tubular activation member 30 such that when the cap 10 is manually operated and detached, it allows the tubular activation member 30 to be moved by the force from the second resilient member 24 (FIG. 1c) from its non-activated position to its activated position.

FIG. 2b show the medicament delivery device 1 when it is ready for use. When a user is about to perform a medicament delivery e.g. an injection he/she presses the proximal end, i.e. the annular contact member 31, against the delivery site e.g. an injection site. The tubular activation member 30 is then moved in the distal direction, in relation to the tubular housing 20, and during the relative movement when having a medicament delivery device as an injection device, then a needle 61 manually penetrates the skin. When the tubular activation member 30 is about to reach its most distal position in relation to the tubular housing 20 the medicament delivery is performed. A medicament delivery is automatically performed when the tubular activation member 30, being in an activated position, is moved in a distal direction in relation to the tubular housing 20, to a delivery state position, where the annular contact member 31 is close to the proximal end 11 of the tubular housing 20.

FIG. 2c illustrates when the delivery is made, then the user removes the medicament delivery device 1 from the delivery site, thereby allowing the tubular activation member 30 to move in the proximal direction in relation to the tubular housing 20, by the force exerted by the second resilient member 24 and finally reaches a final state; the locked state.

FIG. 2d illustrates the medicament delivery device 1 in its final and locked state, wherein the tubular activation member 30 once more is in its most proximal position. As illustrated, in this final and locked state the proximal part of the tubular activation member 30 fully protects the delivery member 61 and the tubular activation member 30 is also locked, by the cut-out/recesses 36 (see FIG. 1b) in the distal end of the tubular activation member 30, engaging with the protrusions (not illustrated) of the tubular housing 20, in the final position in order to prevent unintentional availability of the delivery member 61.

Figure 3:
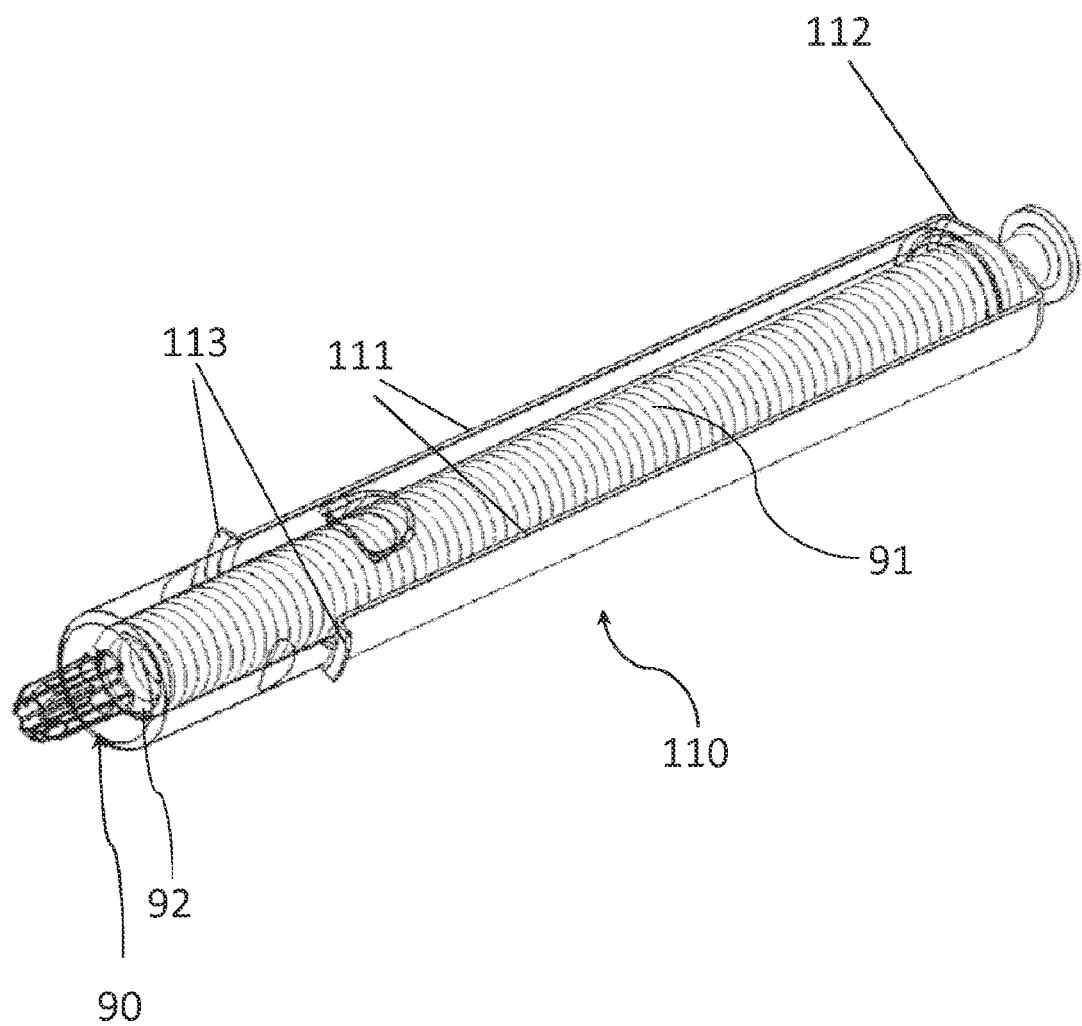
FIG. 3 illustrates a plunger rod and audio-tacit-visual signal generating member assembly.

FIG. 3 illustrates various aspects of the feedback means, such as a signal generating member 110 and its implementations (see also FIG. 4a-FIG. 4c). In FIG. 3 is illustrated an embodiment of the invention comprising the signal generating member 110 adapted to generate an audible and/or tactile and/or visible injection confirmation signal upon a performed medicament delivery, wherein the medicament delivery confirmation signal is generated when the drive means changes state from a pre-tensioned state wherein the first resilient member is pretensioned arranged within the plunger rod and the plunger rod is engaged to the tubular extension part, to a released state wherein the plunger rod is completely released from the tubular extension part and is no longer in contact with the signal generating member.

FIG. 4a-FIG. 4c illustrates a side view and perspective views, respectively, of the signal generating member 110 according to an exemplary embodiment of the invention. In the illustrated embodiment, the signal generating member 110 is an elongated u-shaped bracket, provided with at least two elongated arms 111, directed in the proximal direction, and a lower part, a distal transversal end wall, 112 directed in the distal direction of the medicament delivery device, when arranged within the tubular extension part 22. The signal generating member 110 may be made from metal, plastic, or any combination of these materials.

FIG. 4c is a perspective, and partly exploded, view of the signal generating member 110 in relation to the plunger rod 90 and the first resilient member 91. The upper parts of the arms 111 are provided with angled support members 113 extending in essentially radial outward directions with regard to a longitudinal axis of the u-bracket 110. The u-bracket 110 is adapted to enclose at least a part of the plunger rod 90 and the first resilient member 91, and the support members 113 are adapted to rest on an annular surface on the proximal end of the tubular extension part 22 when the drive means are in a pre-tensioned state, i.e. the opening 94 of the plunger rod 90 is engaged with a radial inward projected protrusion (not shown) of a flexible tongue 121 of the tubular extension part 22.

When the drive means is in the pre-tensioned state, the distal end of the u-bracket 110 is arranged at a predetermined distance "D" (see FIG. 6a) from an inner distal surface of said tubular extension part 22 and when the drive means are in the released state, the distal end of the u-bracket 110 is in contact with the inner distal surface of said tubular extension part 22. The audible and/or tactile and/or visible confirmation signal is generated when the distal end of the u-bracket 110 hits and contacts the inner distal surface of the tubular extension part 22 by a remaining force exerted by said first resilient member 91. Thus, during the delivery procedure, when the distal end of the plunger rod 90 passes by the supporting members 113, the arms 111 with the support members 113 are released and allowed to move in a radial inward direction, due to a pre-tension of the arms 111, enabling the u-bracket 110 to move in the distal direction and the signal, typically an audible sound and/or a visual signal and/or a tactile signal is generated, when the u-bracket 110 hits the distal end of the tubular extension part 22. In the pre-injection state the u-bracket 110 is arranged such that the arms 111 are positioned in a space along the plunger rod 90 between the plunger rod 90 and the tubular extension part 22 enclosing the plunger rod 90. The support members 113 must have an extension in the radial outward direction that exceeds the radial extension of the space between the plunger rod 90 and the inner wall of the tubular extension part 22 to secure that the signal generating member 110 is not released prior the plunger rod 90 has moved away from between the arms 111. the outer distal surface of the distal transversal end wall 112 may further have a protrusion (not illustrated), adapted to be guided through an opening, typically a through hole (also not illustrated) of the distal end wall of the tubular extension part 22 and extends distally a predetermined distance over the outer surface of said tubular extension part 22. In an exemplary embodiment of the invention, the distally extending protrusion has a bright and/or different colour than the rest of the device for generating a visual signal. Thus, said protrusion will enable both a tactile and a visual signal when the u-bracket 110 hits the distal end of the tubular extension part 22.

Figure 5:
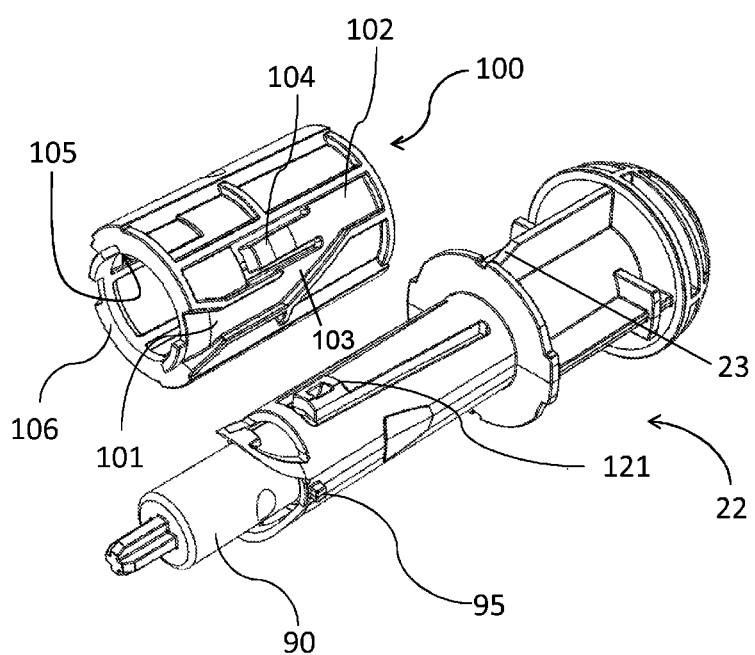
FIG. 5 shows a perspective view of a driving means comprised in the present invention.

FIG. 5 illustrates the drive means as well as the holding means, wherein the holding means comprises the tubular operation member 100 and the tubular extension part 22. The above-mentioned first corresponding co-acting means 35 are at least one inwards extending protrusion (see FIG. 1b) on the distal end of the inner surface of the tubular activation member 30 and the second co-acting means are at least one groove 101, 102, 103 on an outer surface of the tubular operation member 100, such that said radial inwards extending protrusion 35 is adapted to be guided within the at least one groove 101, 102, 103, forcing the tubular operation member 100 to rotate when the tubular activation member 30 is axially moved. A co-acting means for holding the plunger rod 90 and the first resilient member 91 in the pre-tensioned state comprises at least one groove 105 of the tubular operation member 100 and engages with a flexible tongue 121 on the tubular extension part 22, which locks the plunger rod 90 by the radial inwards extending protrusion (not shown) of the flexible tongue 121 and engaging with the opening 94 of the plunger rod 90. When the tubular operation member 100 is rotated, at least one groove 105 of the tubular operation member 100 allows the radial inwards extending protrusion of the flexible tongue 121 to radial extension, thereby releasing the engagement between the protrusion and the opening 94 of the plunger rod 90, thus releasing the plunger rod 90, exerted by the force of the first resilient member 91, in a proximal direction.

The medicament delivery device 1 further comprises a locking means interactively connected to the tubular activation member 30. The locking means is preferably at least one ledge 106 on an annular surface of the tubular operation member 100 and a corresponding locking means are at least one protrusion 95 on an outer surface of the tubular extension part 22, such that said at least one protrusion 95 is abutting said at least one ledge 106 holding the tubular operation member 100 rotable fixatied to the tubular extension part 22.

Figure 6A:
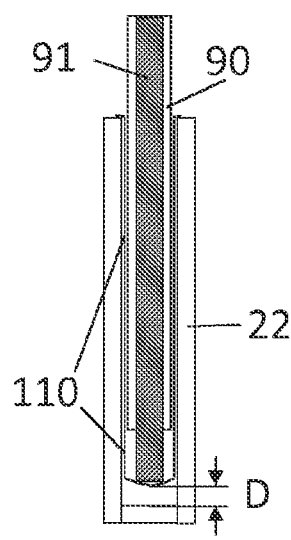
FIGS. 6a, 6b and 6c show a side view of the tubular housing and the audio-tacit-visual signal generating member in operation.
Figure 6B:
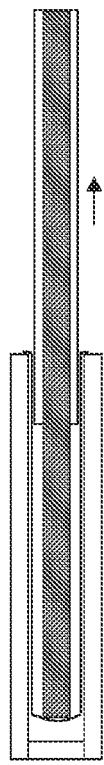
Figure 6C:
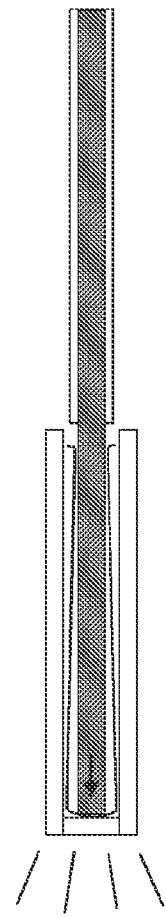

FIG. 6a-FIG. 6c illustrates simplified side views of the distal part of the medicament delivery device 1 according to the present invention. The purpose of these figures is to briefly describe and illustrate the important features required to achieve the stated objects. In the figures are shown the tubular extension part 22 that partly encloses the drive means, i.e. the plunger rod and the first resilient member 91, and the signal generating member 110.

In FIG. 6a the medicament delivery device 1 is ready for use, wherein the signal generating member 110 is at a predetermined distance "D" from the inner distal surface of the tubular extension part 22.

In FIG. 6b the delivery procedure is initiated and the plunger rod 90 moves in the proximal direction forcing the slidable stopper 83 (not shown) to expel the medicament via the delivery member 61. When the distal end of the plunger rod 90 has passed the proximal part of the signal generating member 110 the arms 111 of the signal generating member 110 flexes inwards allowing the signal generating member 110 to move in the distal direction, resulting in that a sound, and/or a tactile signal and/or a visual signal is generated when the signal generating member 110 contacts the inner distal surface of the tubular extension part 22. This is illustrated by FIG. 6c.

FIG. 7-FIG. 11 show side views along the longitudinal axis of the medical delivery device 1. For sake of simplicity only features relevant for describing the signal generation are indicated; in addition some main parts of the medical delivery device 1 are indicated in FIG. 7-FIG. 11.

Figure 7:
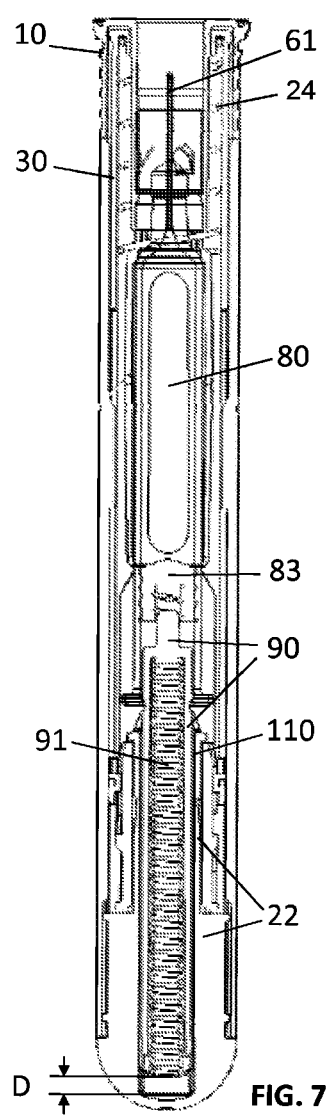
FIGS. 7, 8, 9, 10 and 11 show side views along the longitudinal axis of the medicament delivery device according to an embodiment of the present invention, illustrating different states of an injection procedure.
Figure 8:
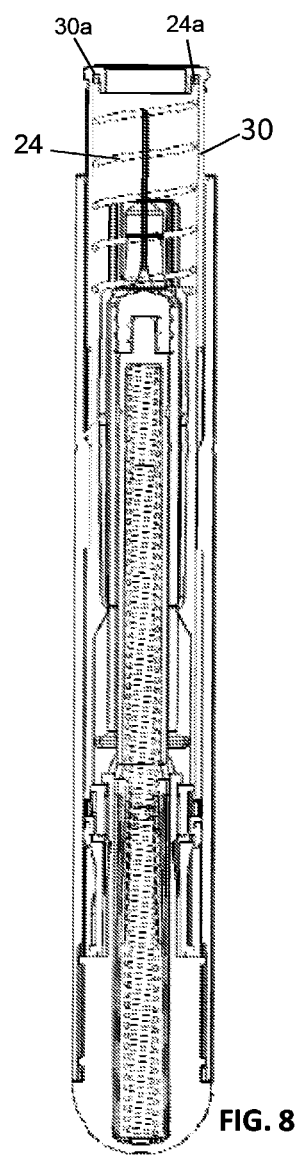

FIG. 7 shows the medicament delivery device in an initial state where the cap 10 is still attached to the medicament delivery device. The container 80 is arranged within the medicament delivery device having a predetermined volume of medicament and also provided with a delivery member 61 and a slidable stopper 83 at its distal end. As illustrated in FIG. 8, the second resilient member 24 has a terminal proximal end 24a that abuts and is arranged in an inside ledge 30a positioned at the proximal end of the medicament delivery device applying a force to the tubular activation member 30 in the proximal direction. The plunger rod 90 has a proximal end in contact with the slidable stopper 83 and encloses, at least partly, the first resilient member 91 which is adapted to apply a force to the plunger rod 90 in the proximal direction. The distal part of the plunger rod 90 is arranged in the tubular extension part 22 in combination with the signal generating member 110. In the most distal part of the medicament delivery device 100 is indicated the distance "D", i.e. the "sound-generating" distance between the distal part of the signal generating member 110 and the inner distal surface of the tubular extension part 22.

FIG. 8 shows the medicament delivery device in the final locked state, where the tubular activation member 30 is locked in its proximal position, protecting the delivery member 61.

Figure 9:
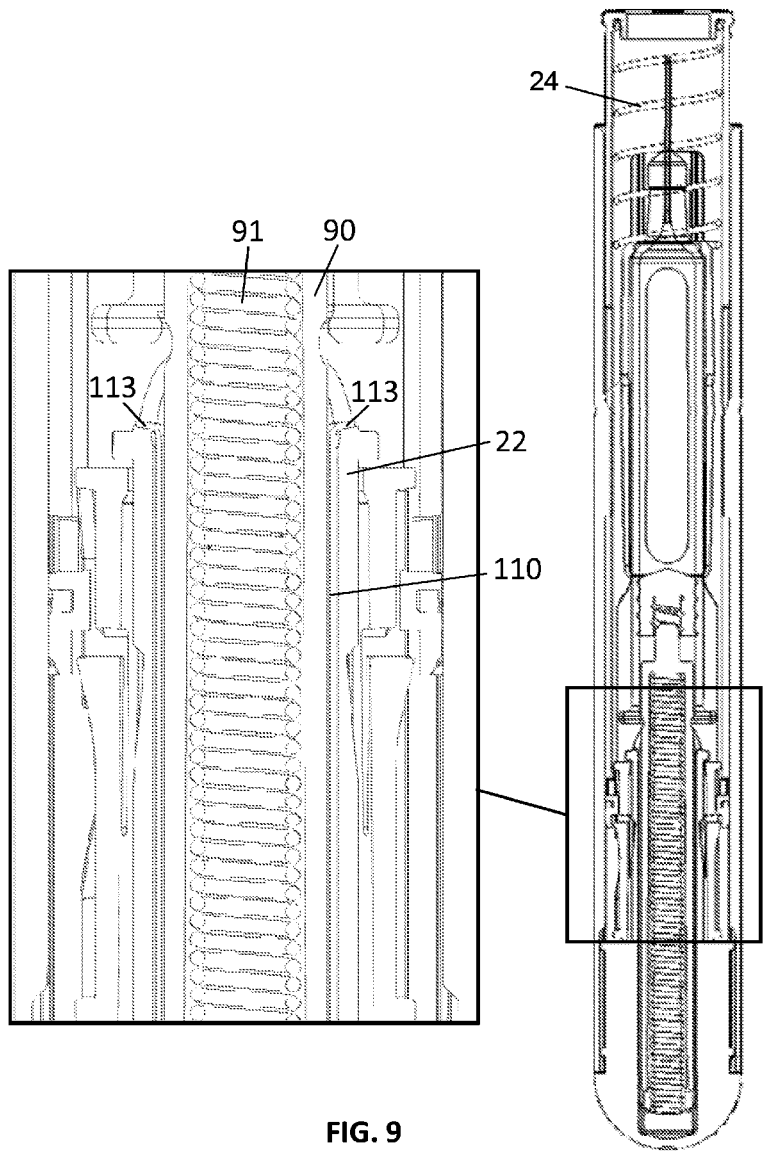

FIG. 9 shows the medicament delivery device where the cap 10 has been removed from the medicament delivery device resulting in that the tubular activation member 30 is moved forward due to the forces exerted by the second resilient member 24. In the figure is shown in greater scale the proximal part of the signal generating member 110 and its support members 113.

Figure 10:
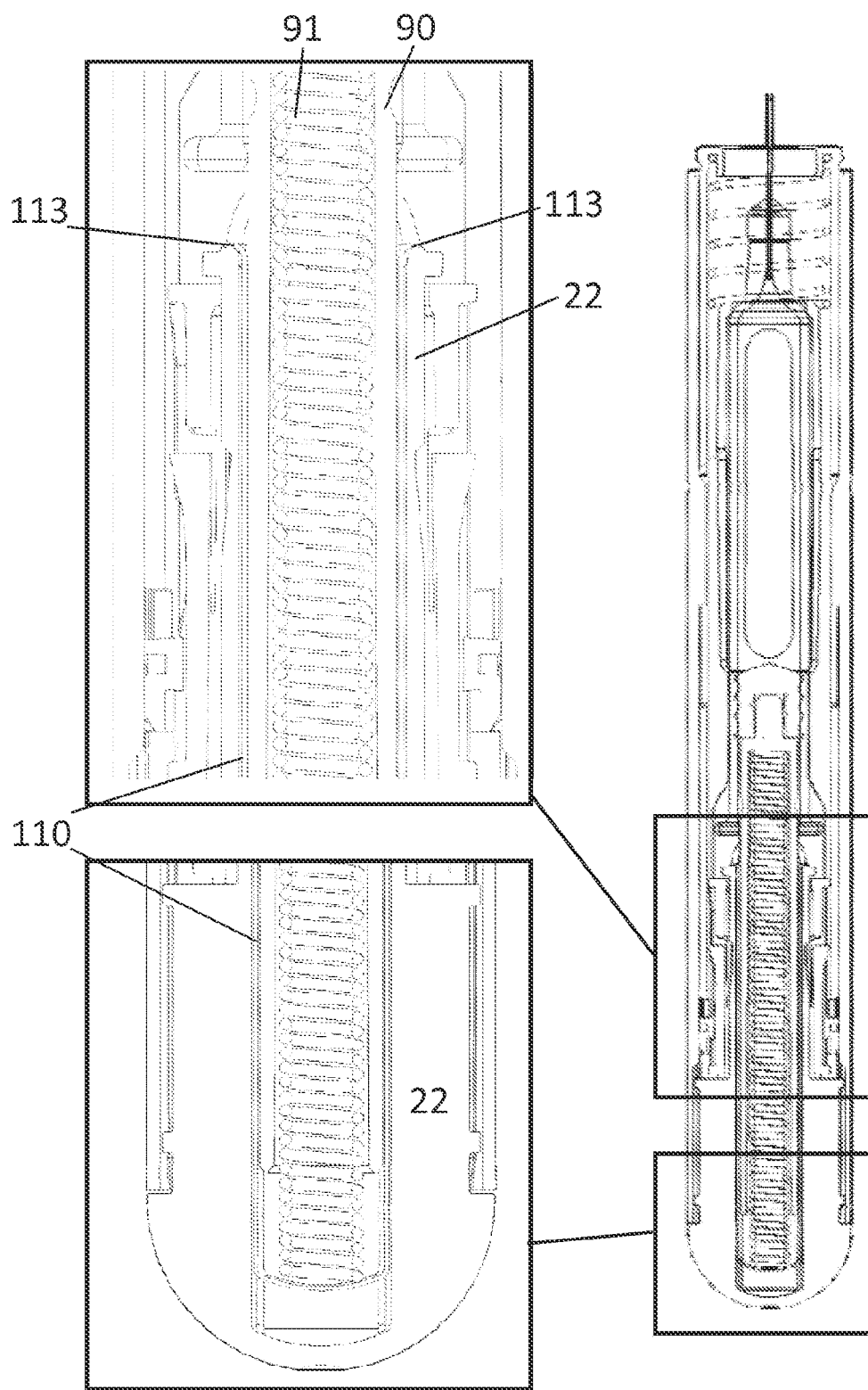

FIG. 10 shows the medicament delivery device where the tubular activation member 30 is forced in the distal direction resulting in that the plunger rod 90 is released to be able to apply forces to the slidable stopper 83 resulting in that the medicament is delivered. In the figure is shown in greater scale the proximal part of the signal generating member 110 and its support members 113 and also the most distal part of the medicament delivery device.

Figure 11:
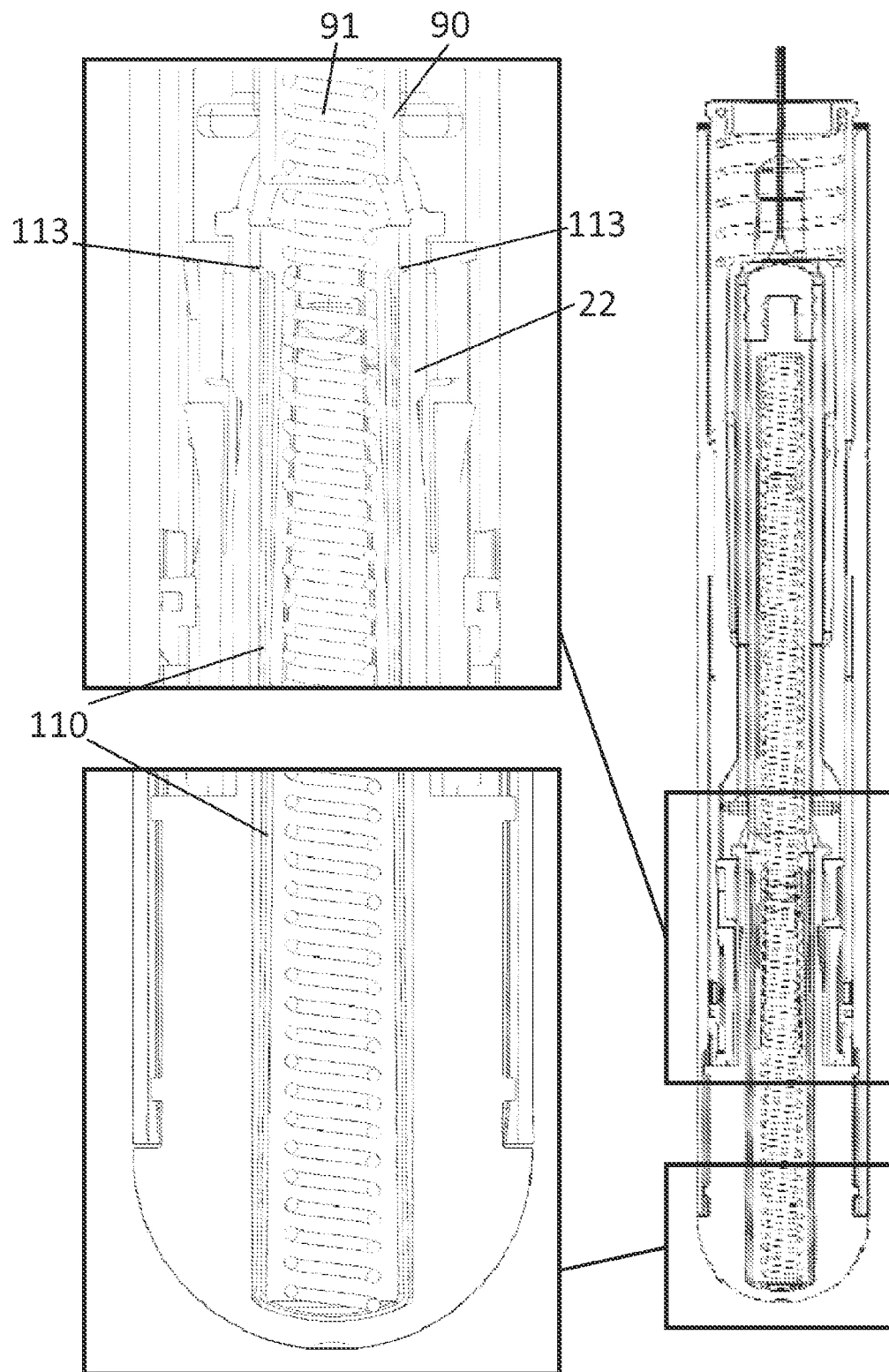

FIG. 11 shows the medicament delivery device where the delivery has been made. The plunger rod 90 has now forced the slidable stopper 83 to expel all medicament from the container 80 through the delivery member 61. When the distal part of the plunger rod 90 passes by the distal part of the signal generating member 110 the arms 111 are allowed to move inwards due to the pre-tension of the arms (illustrated by the upper in-zoomed part) and the signal generating member 110 is released and moves thereby in the distal direction generating a signal, when reaching the distal end surface of the tubular extension part 22 (illustrated by the lower in-zoomed part).

Thus is illustrated a signal generating member 110 provided with two arms 111. As indicated above, a higher number of arms is naturally possible within the scope of the present invention as defined by the appended claims. if a higher number of arms is considered, e.g. three or four, it is important that they all are pre-tensioned such that they exert radially inward directed forces and also that they are evenly distributed in a cross-sectional plane of the signal generating member 110 in order to securely hold drive means in the pre-tensioned state.

With references mainly to FIG. 7 to FIG. 11 the operation of the medicament delivery device 1 will now be described in more detail. In the pre-tensioned state, the at least one protrusion is abutting the ledge 106 and the groove 105 is not aligned with the flexible tongue 121 that is preventing release of the plunger rod 90. When the cap 10 is removed the medicament delivery device 1 is ready for use. The tubular activation member 30 is now in its most proximal position and the medicament delivery device 1 is ready for use. The tubular activation member 30 is forced in the distal direction by the user and the protrusion 35 is moved along the groove from position 101 to 103 to position 102 achieving an anticlockwise rotation of the tubular operation member 100, seen from the distal end. During the rotation of the tubular operation member 100 the protrusion 95 is moved along the ledge 106 and finally comes off the ledge 106. Alignment of groove 105 with flexible tongue 121 enables the release of the pre-tensioned plunger rod 90 to move in the proximal direction, by the force exerted by the first resilient member 91, and to apply forces to the slidable stopper 83 that is forced to move in the proximal direction and the medicament is thus delivered. When the medicament has been delivered and the medicament delivery device is removed from the delivery site, the tubular activation member 30 is forced in the proximal direction, by means of the second resilient member 24 and the locking means, e.g. a flexible tongue 104 (see FIG. 5), on the at least one groove of the tubular operation member 100 which locks the radially inwards extending protrusion 35 when the radially inwards extending protrusion 35 is moved over the tongue 104. The medicament delivery device 1 further comprises a locking means interactively connected to the tubular activation member 30. The locking means is a flexible tongue 104 on the at least one groove of the tubular operation member 100 which locks the radially inwards extending protrusion 35 when said radially inwards extending protrusion is moved over the tongue 104.

The generation of the signal functions as follows. When the drive means is in the pre-tensioned state, the distal end of the u-bracket 110 is arranged at a predetermined distance "D" (see FIG. 6a) from an inner distal surface of said tubular extension part 22 and when the drive means are in the released state, the distal end of the u-bracket 110 is in contact with the inner distal surface of said tubular extension part 22. The audible and/or tactile and/or visible confirmation signal is generated when the distal end of the u-bracket 110 hits and contacts the inner distal surface of the tubular extension part 22 by a remaining force exerted by said first resilient member 91. Thus, during the delivery procedure, when the distal end of the plunger rod 90 passes by the supporting members 113, the arms 111 with the support members 113 are released and allowed to move in a radial inward direction, due to a pre-tension of the arms 111, enabling the u-bracket 110 to move in the distal direction and the signal, typically an audible sound and/or a visual signal and/or a tactile signal is generated, when the u-bracket 110 hits the distal end of the tubular extension part 22. In the pre-injection state the u-bracket 110 is arranged such that the arms 111 are positioned in a space along the plunger rod 90 between the plunger rod 90 and the tubular extension part 22 enclosing the plunger rod 90. The support members 113 must have an extension in the radial outward direction that exceeds the radial extension of the space between the plunger rod 90 and the inner wall of the tubular extension part 22 to secure that the signal generating member 110 is not released prior the plunger rod 90 has moved away from between the arms 111. the outer distal surface of the distal transversal end wall 112 may further have a protrusion (not illustrated), adapted to be guided through an opening, typically a through hole (also not illustrated) of the distal end wall of the tubular extension part 22 and extends distally a predetermined distance over the outer surface of said tubular extension part 22. In an exemplary embodiment of the invention, the distally extending protrusion has a bright and/or different colour than the rest of the device for generating a visual signal. Thus, said protrusion will enable both a tactile and a visual signal when the u-bracket 110 hits the distal end of the tubular extension part 22.

It is however to be understood that embodiments described above and shown in the drawings are to be regarded only as non-limiting examples of the present invention and that may be modified within the scope of the appended patent claims.

The invention claimed is:

1. A medicament delivery device comprising:
 a housing having a proximal end;
 a pre-filled syringe positioned within the housing and comprising a needle, a dose of medicament and a sliding stopper, wherein the syringe is axially fixed relative to the housing during a delivery of the dose of medicament through the needle such that a proximal end of the needle remains axially fixed relative to the housing before and after the delivery of the dose of medicament;
 a tubular activation member comprising two distally projecting arms and a proximal end portion terminating in a radial flange comprising an inside ledge, where the tubular activation member is slidably positioned within the housing to move from a first position to a second position and then to a final locked position;
 a spring located in the proximal end portion of the tubular activation member such that a terminal proximal end of the spring abuts the inside ledge, where the spring is in a compressed state when the tubular activation member is in the second position;
 a plunger rod operatively connected to the stopper, where the plunger rod can only move proximally relative to the tubular activation member when the tubular activation member is in the second position;
 wherein each of the distally projecting arms comprises a distal portion that forms a lock when the tubular activation member is in the final locked position such that the tubular activation member is prevented from moving distally relative to the housing to expose the axially fixed needle, and
 wherein the radial flange is positioned outside of the proximal end of the housing when the tubular activation member is in the first position, the second position, and the final locked position.

2. The delivery device of claim 1, wherein the proximal end portion of the tubular activation member extends longitudinally from the radial flange and has an outer diameter.

3. The delivery device of claim 2, where the radial flange comprises a terminal end face having a diameter greater than the outer diameter of the proximal end portion.

4. The delivery device of claim 1, wherein the radial flange has a terminal end face configured for direct contact with an injection site.

5. The delivery device of claim 1, wherein the spring is positioned inside the tubular activation member to bias the proximal end portion of the tubular activation member proximally when the tubular activation member is in the first position.

6. The delivery device of claim 1, wherein the housing has an outer surface and the proximal end portion of the tubular activation member extends distally and longitudinally from the radial flange, where the tubular activation member slides relative to the outer surface when the tubular activation member moves from the first position to the second position and then to the final locked position.

7. The delivery device of claim 1, wherein the proximal end of the needle protrudes beyond a terminal end face of the radial flange when the tubular activation member is in the second position.

8. The delivery device of claim 1, wherein the tubular activation member further comprises a protrusion located at a distal end that forms a part of the lock when the tubular activation member is the final locked position.

9. The delivery device of claim 1, wherein the tubular activation member is rotationally fixed relative to the housing.

10. The delivery device of claim 1, wherein the tubular activation member further comprises a distal end comprising a protrusion.

11. A medicament delivery device comprising:
 a housing having a proximal end;
 a pre-filled syringe positioned within the housing and comprising a needle having a proximal end, where the syringe is axially fixed relative to the housing during a delivery of a medicament through the needle such that the proximal end of the needle remains axially fixed relative to the housing before and after the delivery of the medicament;
 a tubular activation member comprising two distally projecting arms and a proximal end portion terminating in a radial flange comprising an inside ledge, where the tubular activation member is slidably positioned within the housing to move from a first position to a second position and then to a final locked position, where the radial flange is positioned proximal of the proximal end of the needle when the tubular activation member is in the first position and the final locked position;

a spring located in the proximal end portion of the tubular activation member such that a terminal proximal end of the spring abuts the inside ledge, where the spring is in a compressed state when the tubular activation member is in the second position such that the proximal end portion is biased to axially move in a proximal direction as the tubular activation member slidably moves from the second position to the final locked position;

wherein each of the distally projecting arms comprises a distal portion that forms a lock when the tubular activation member is in the final locked position such that the tubular activation member is prevented from moving distally relative to the housing to expose the axially fixed needle, and wherein the radial flange is positioned outside of the proximal end of the housing when the tubular activation member is in the first position, the second position, and the final locked position.

12. A medicament delivery device comprising:

a housing having a proximal end;

a pre-filled syringe positioned within the housing and comprising a needle, a dose of medicament and a sliding stopper, where the syringe is axially fixed relative to the housing during a delivery of the dose of medicament through the needle such that a proximal end of the needle remains axially fixed relative to the housing before and after the delivery of the dose of medicament;

a tubular activation member comprising two distally projecting arms and a proximal end portion having an outer diameter and terminating in a radial flange comprising an inside ledge, where the tubular activation member is slidably positioned within the housing to move from a first position to a second position and then to a final locked position;

a spring located in the proximal end portion of the tubular activation member such that a terminal proximal end of the spring abuts the inside ledge, where the spring is in a compressed state when the tubular activation member is in the second position such that the proximal end portion is biased to axially move in a proximal direction as the tubular activation member slidably moves from the second position to the final locked position;

wherein each of the distally projecting arms comprises a distal portion that forms a lock when the tubular activation member is in the final locked position such that the tubular activation member is prevented from moving distally relative to the housing to expose the axially fixed needle, wherein the radial flange is positioned outside of the proximal end of the housing when the tubular activation member is in the first position, the second position, and the final locked position, wherein the spring is positioned inside the tubular activation member to bias the proximal end portion of the tubular activation member proximally when the tubular activation member is in the first position, and where the radial flange comprises a terminal end face having a diameter greater than the outer diameter of the proximal end portion.

13. The delivery device of claim 12, where the radial flange is positioned proximal of the proximal end of the needle when the tubular activation member is in the first position and the final locked position.

* * * * *